United States Patent
Kim et al.

(10) Patent No.: US 7,584,666 B2
(45) Date of Patent: Sep. 8, 2009

(54) PRESSURE SENSOR FOR MEASURING BLOOD PRESSURE AND METHOD OF FABRICATING THE SAME

(75) Inventors: Jong-pal Kim, Seoul (KR); Kun-soo Shin, Seongnam-si (KR); Sang-kon Bae, Seongnam-si (KR); Youn-ho Kim, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 11/968,665

(22) Filed: Jan. 3, 2008

(65) Prior Publication Data

US 2009/0013793 A1 Jan. 15, 2009

(30) Foreign Application Priority Data

Jul. 9, 2007 (KR) .................... 10-2007-0068819

(51) Int. Cl.
*G01L 9/06* (2006.01)

(52) U.S. Cl. .............................. 73/727; 73/753; 73/754; 128/897

(58) Field of Classification Search ........... 73/700–756; 361/283.1–283.4; 128/897–899
See application file for complete search history.

(56) References Cited

U.S. PATENT DOCUMENTS

| | | | |
|---|---|---|---|
| 5,083,466 A * | 1/1992 | Holm-Kennedy et al. ..................... 73/862.041 |
| 5,095,762 A * | 3/1992 | Holm-Kennedy et al. ..................... 73/862.041 |
| 5,101,669 A * | 4/1992 | Holm-Kennedy et al. ..................... 73/862.626 |
| 5,109,701 A * | 5/1992 | Jacobsen et al. .............. 73/782 |
| 5,379,640 A * | 1/1995 | Yamamoto ............... 73/514.14 |
| 5,444,244 A * | 8/1995 | Kirk et al. ...................... 850/9 |
| 5,559,291 A * | 9/1996 | Hasegawa ................ 73/504.12 |
| 5,686,711 A * | 11/1997 | Yamamoto ............... 200/61.48 |
| 5,771,902 A * | 6/1998 | Lee et al. ..................... 128/897 |
| 6,000,280 A * | 12/1999 | Miller et al. .................. 73/105 |
| 6,073,484 A * | 6/2000 | Miller et al. .................. 73/105 |
| 6,479,920 B1 * | 11/2002 | Lal et al. ..................... 310/309 |
| 6,787,804 B1 * | 9/2004 | Yang ........................... 257/62 |
| 7,032,454 B2 * | 4/2006 | Amano ........................ 73/704 |
| 7,104,134 B2 * | 9/2006 | Amano et al. ................. 73/704 |
| 7,428,841 B2 * | 9/2008 | Harada et al. ................. 73/509 |
| 7,461,559 B2 * | 12/2008 | Takizawa ..................... 73/777 |

FOREIGN PATENT DOCUMENTS

JP 2000-214027 A 8/2000
JP 2004-279090 A 10/2004

* cited by examiner

*Primary Examiner*—Andre J Allen
*Assistant Examiner*—Jermaine Jenkins
(74) *Attorney, Agent, or Firm*—Sughrue Mion, PLLC

(57) ABSTRACT

A pressure sensor includes at least one cantilever formed on an upper surface of a silicon substrate, a piezoresistor formed on a fixed end of the cantilever, and a metal wire and an electrode pad connected to both ends of the piezoresistor, wherein a stopper that limits a deformation of a free end of the cantilever is formed below the cantilever.

16 Claims, 7 Drawing Sheets

PRESSURE SENSOR FOR MEASURING BLOOD PRESSURE AND METHOD OF FABRICATING THE SAME

CROSS-REFERENCE TO RELATED PATENT APPLICATION

This application claims the benefit of Korean Patent Application No. 10-2007-0068819, filed on Jul. 9, 2007, in the Korean Intellectual Property Office, the disclosure of which is incorporated herein in its entirety by reference.

BACKGROUND OF THE INVENTION

1. Field of the Invention

The present invention relates to a pressure sensor for measuring blood pressure, and more particularly, to a pressure sensor used in a tonometry method for measuring blood pressure, and a method of fabricating the pressure sensor.

2. Description of the Related Art

Blood pressure is classified into artery blood pressure, capillary blood pressure, and vein blood pressure. Generally, blood pressure indicates the artery blood pressure that varies according to heartbeat.

In a tonometry method, which is one of the methods of consecutively and non-invasively measuring blood pressure, blood pressure is measured by pressing a pressure sensor in a direction toward a radial artery after locating the pressure sensor on the radial artery of the wrist. A sensing unit of the pressure sensor deforms due to blood pressure, and thus, the blood pressure is measured by measuring the deformation of the sensing unit.

The pressure sensor for measuring blood pressure outputs an electrical signal as a pressure value, and the electrical signal is processed by a signal processing system so as to be read as blood pressure. The pressure sensor and the signal processing system constitute a blood pressure measuring system.

A diaphragm pressure sensor has been disclosed in Japanese Patent Publication Nos. 2000-214027 and 2004-279090. The diaphragm pressure sensor has a structure in which a piezometer is formed on an upper part of single crystal silicon having a (100) crystal surface after a lower part of the single crystal silicon is etched. FIG. 1 is a conceptual drawing of the diaphragm pressure sensor.

Referring to FIG. 1, a single crystal silicon substrate 20 is disposed on a glass substrate 10. The surface of the single crystal silicon substrate 20 has a (100) crystal direction, and a sensing unit 30 is formed by anisotropically wet-etching a lower part of the single crystal silicon substrate 20 using KOH or TMAH. The sensing unit 30 includes piezoresistors 40. A diameter of a radial artery is approximately 1.2 mm or higher.

If the single crystal silicon substrate 20 has a thickness of 500 μm, an angle formed by the anisotropical wet-etching of the single crystal silicon substrate 20 is 54.7 degrees. Thus, a width W of an inclined part formed by etching is approximately 350 μm. Accordingly, if a plurality of pressure sensors are arranged in an array, a dead width between adjacent pressure sensors is approximately 700 μm or higher, and thus, it is difficult to use the pressure sensors as an array pressure sensor. Also, a structure for preventing the sensing unit 30 from excessive deformation is not included. Also, in order to form the sensing unit 30 having a uniform thickness, for example, 10 μm, by wet etching for a long time from a lower part of the single crystal silicon substrate 20, a silicon wafer must have a uniform thickness, and a manufacturing process for forming, for example, wires (not shown) at an upper surface of the single crystal silicon substrate 20 as well as the lower part of the silicon substrate 20, is necessary. Also, the lower part of the single crystal silicon substrate 20 and the glass substrate 10 must be bonded.

SUMMARY OF THE INVENTION

To address the above and/or other problems, the present invention provides a blood pressure monolithic pressure sensor that has a reduced dead width and a stopper for preventing a sensing unit from being deformed, and does not require bonding with an additional substrate.

The present invention also provides a method of fabricating the blood pressure monolithic pressure sensor.

According to an aspect of the present invention, there is provided a pressure sensor for measuring blood pressure, comprising: at least one cantilever formed on an upper surface of a silicon substrate; a piezoresistor formed on a fixed end of the cantilever; and a metal wire and an electrode pad connected to both ends of the piezoresistor, wherein a stopper that limits a deformation of a free end of the cantilever is formed below the cantilever.

The silicon substrate may be a single crystal silicon having a (111) crystal surface on an upper surface thereof.

The cantilever may have a width of 10 to 500 μm, and a depth from the cantilever to the stopper may be 1 to 50 μm.

The cantilever may comprise a plurality of cantilevers, and the plurality of cantilevers may be parallel to each other.

The cantilever may extend in an opposite direction with respect to an adjacent cantilever.

The cantilever may comprise a cantilever pair facing each other.

The silicon substrate, the cantilevers, and the stopper are formed in a monolithic structure.

According to another aspect of the present invention, there is provided a pressure sensor for measuring blood pressure, comprising: at least one beam formed on an upper surface of a silicon substrate, wherein both ends of the beam are supported by the silicon substrate; piezoresistors formed on both ends of the beam; and a wire and an electrode pad connected to both ends of each of the piezoresistors, wherein a stopper that limits a deformation of the beam is formed below the beam.

According to an aspect of the present invention, there is provided a method of fabricating a pressure sensor, comprising: (a) forming a piezoresistor on a fixed end of cantilever forming region on an upper surface of a silicon substrate;

(b) forming a wire and an electrode pad connected to both ends of the piezoresistor;

(c) forming an insulating layer that exposes a first region that defines the cantilever forming region on the silicon substrate;

(d) etching the silicon substrate to a predetermined depth from a surface of the first region of the silicon substrate;

(e) forming a wall protective film on a side wall of the etched first region;

(f) forming a first wall where the wall protective film is not formed by dry etching the first region of the silicon substrate exposed through the wall protective film to a predetermined depth; and (g) forming a cantilever and a stopper that limit a deformation of the cantilever by etching the first wall exposed through the wall protective film.

The forming of the piezoresistor may comprise implanting a p-type dopant in the fixed end of the cantilever forming region.

According to another aspect of the present invention, there is provided a method of fabricating a pressure sensor, comprising: (a) forming piezoresistors on both ends of a both ends supported beam forming region on an upper surface of a silicon substrate;

(b) forming a wire and an electrode pad connected to both ends of the piezoresistor;

(c) forming an insulating layer that exposes a first region that defines the beam forming region on the silicon substrate;

(d) etching the silicon substrate to a predetermined depth from a surface of the first region of the silicon substrate;

(e) forming a wall protective film on a side wall of the etched first region;

(f) forming a first wall where the wall protective film is not formed by dry etching the first region of the silicon substrate exposed through the wall protective film to a predetermined depth; and (g) forming a both ends supported beam and a stopper that limit a deformation of the beam by etching the first wall exposed through the wall protective film.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings in which exemplary embodiments of the invention are shown.

Figure 1:
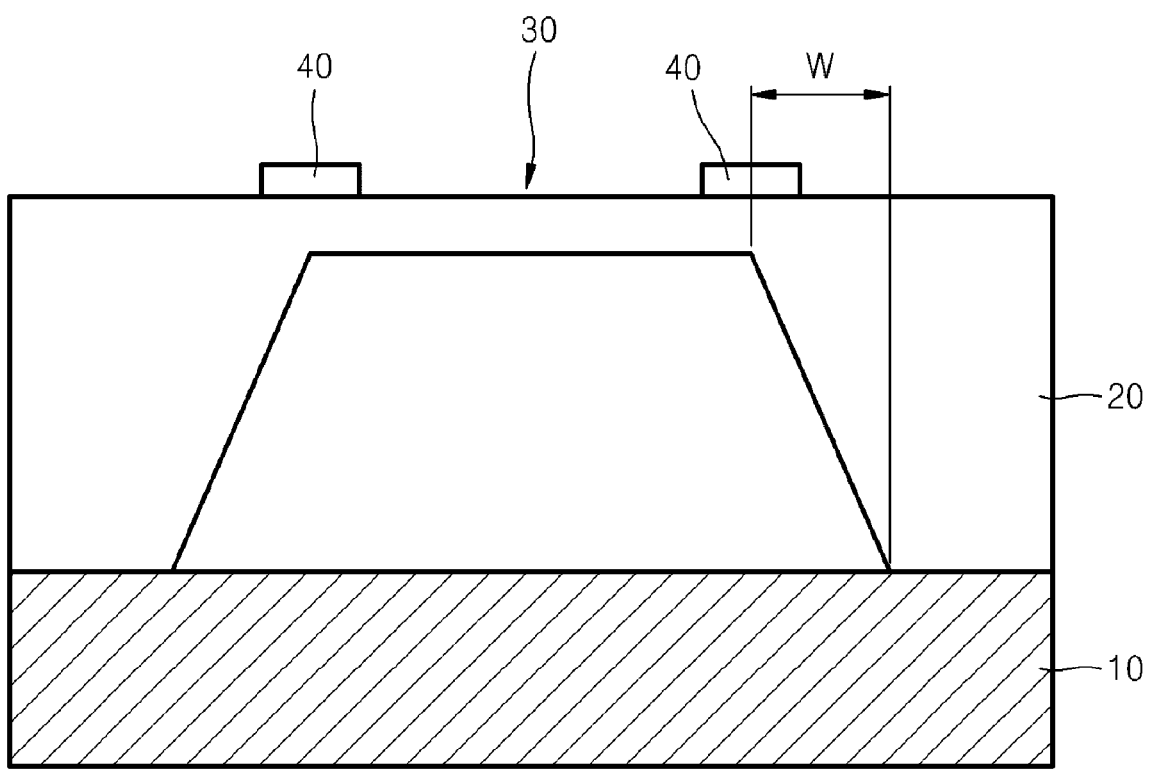
FIG. 1 is a cross-sectional view of a conventional pressure sensor.
Figure 2:
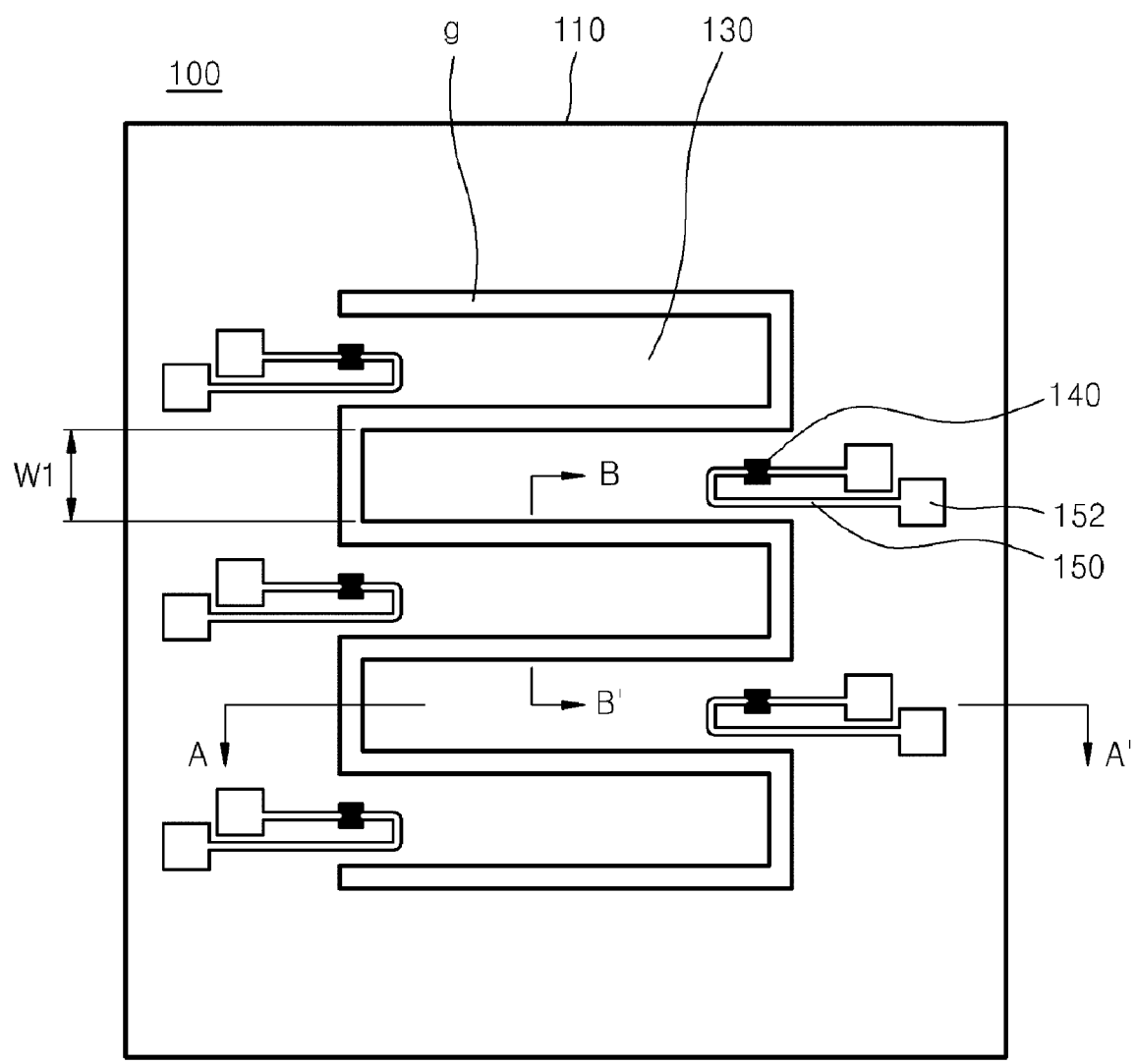
FIG. 2 is a plan view of a pressure sensor for measuring blood pressure, according to an exemplary embodiment of the present invention.
Figure 3:
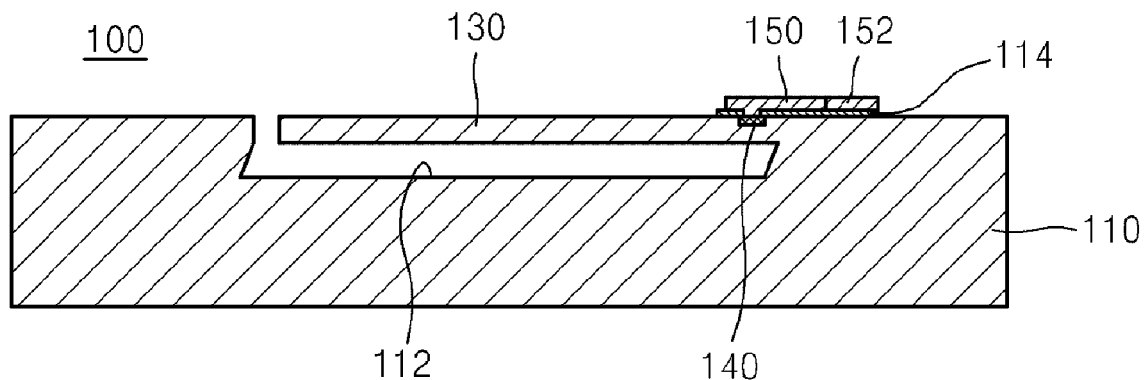
FIG. 3 is a cross-sectional view taken along line A-A' of FIG. 2, according to an exemplary embodiment of the present invention.

FIG. 2 is a plan view of a pressure sensor 100 for measuring blood pressure, according to an embodiment of the present invention. FIG. 3 is a cross-sectional view taken along line A-A' of FIG. 2.

Referring to FIGS. 2 and 3, five cantilevers 130 parallel to each other are formed in an array shape on a silicon substrate 110. A fixed end of each of the cantilevers 130 receives the largest stress when the cantilever 130 is deformed. A piezoresistor 140 is formed on the fixed end of each of the cantilevers 130. In the present embodiment, the silicon substrate 110 is an n-type single crystal silicon substrate having a (111) crystal surface, and the piezoresistor 140 may be a boron implanted p-type region. A wire 150, for example, an Au or Al wire 150, and an electrode pad 152 are connected to both sides of the piezoresistor 140. If a current meter (not shown) is connected to the electrode pad 152, an electrical signal emitted from the piezoresistor 140 may be read, and thus, blood pressure may be measured.

The cantilevers 130 are parallel to each other and adjacent cantilevers 130 extend in an opposite direction from each other. A gap g between the cantilevers 130 and the silicon substrate 110 may be a few μm, and thus, the dead width, which is a problem in the prior art, may be reduced. The cantilevers 130 may be formed to have a width W1 of a few tens to a few hundreds of μm. Considering that the diameter of the radial artery of an adult is 1.2 to 3 mm, the cantilevers 130 may be formed to have a width W1 of 10 to 500 μm. The cantilevers 130 may be formed to have a thickness of 1 to 50 μm.

The wire 150 and the electrode pad 152 may be formed by patterning a metal, for example, Au or Al, after depositing the metal on the silicon substrate 110. An insulating layer 114 may be formed between the substrate 110 and the wire 150 and the electrode pad 152 to insulate the substrate 110 and the wire 150 from the substrate 110.

The pressure sensor 100 according to the present embodiment also includes a stopper 112 that is formed on a location separated by a predetermined distance from the cantilever 130 to prevent the cantilever 130, in particular, the free end of the cantilever 130, from excessive deformation. The stopper 112 may be formed in the process of forming the cantilevers 130, which will be described later. The distance from the cantilever 130 to the stopper 112 may be 1 to 50 μm, however, may vary according to the length of the cantilever 130.

A thin film formed of rubber, polyimide, or silicone may be further formed on a surface of the pressure sensor 100 to prevent the penetration of foreign materials from the outside and to provide soft feeling when the pressure sensor 100 contacts a patient's wrist.

Since the cantilevers 130, the piezoresistors 140, and the stoppers 112 are formed using the silicon substrate 110 by applying a semiconductor fabricating process, the pressure sensor 100 has a monolithic structure.

When each of the cantilevers 130 of the pressure sensor 100 according to the present embodiment is disposed in a lengthwise direction of the radial artery of the wrist, blood pressure may be consecutively measured.

Figure 4A:
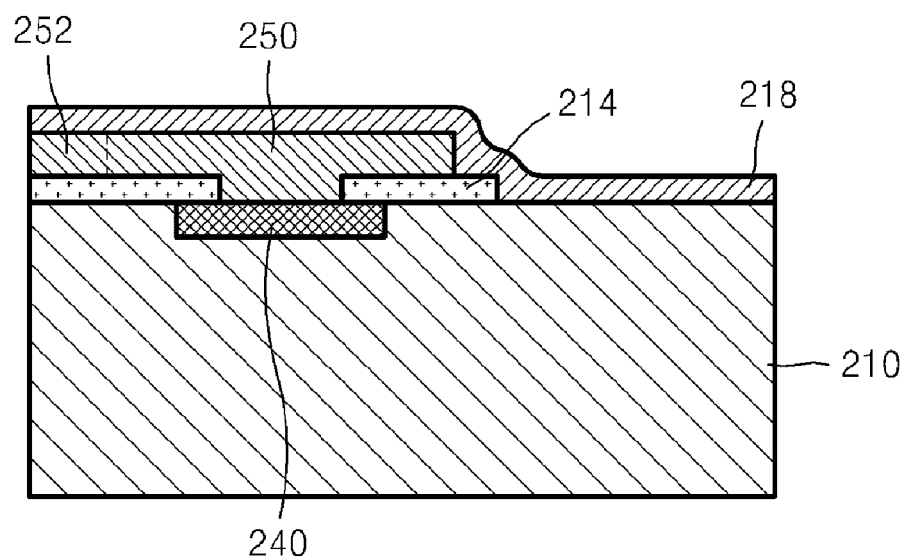
FIGS. 4A through 4E are cross-sectional views for illustrating a method of fabricating a pressure sensor for measuring blood pressure, according to another exemplary embodiment of the present invention.

FIGS. 4A through 4E are cross-sectional views for illustrating a method of fabricating pressure sensor for measuring blood pressure, according to another exemplary embodiment of the present invention. FIG. 4A is a cross-sectional view of a piezoresistor, and FIGS. 4B through 4E are cross-sectional views taken along line B-B' of FIG. 2.

Referring to FIG. 4A, a piezoresistor 240 is formed by implanting boron in a piezoresistor region on an n-type single crystal silicon substrate 210 having a (111) crystal surface. The piezoresistor 240 is a p-type region, can act as a resistor, and corresponds to the piezoresistor 140 of FIG. 2. An insulating layer 214 covering the piezoresistor 240 is formed on the silicon substrate 210. Next, the piezoresistor 240 is exposed by patterning the insulating layer 214. The insulating layer 214 may be formed of silicon nitride.

Next, after depositing a metal, for example, Au or Al, on the silicon substrate 210, wires 250 and electrode pads 252 are formed by patterning the metal layer. The wires 250 are electrically connected to both sides of the piezoresistor 240.

An insulating layer 218, for example, a silicon oxide layer, covering the wire 250 and the electrode pad 252 is formed on the silicon substrate 210.

Figure 4B:
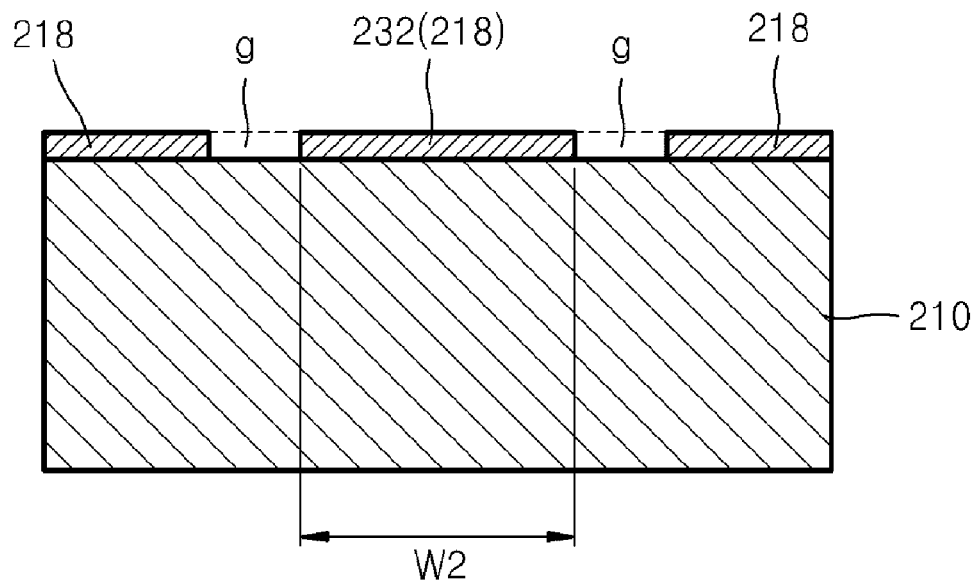
Figure 4C:
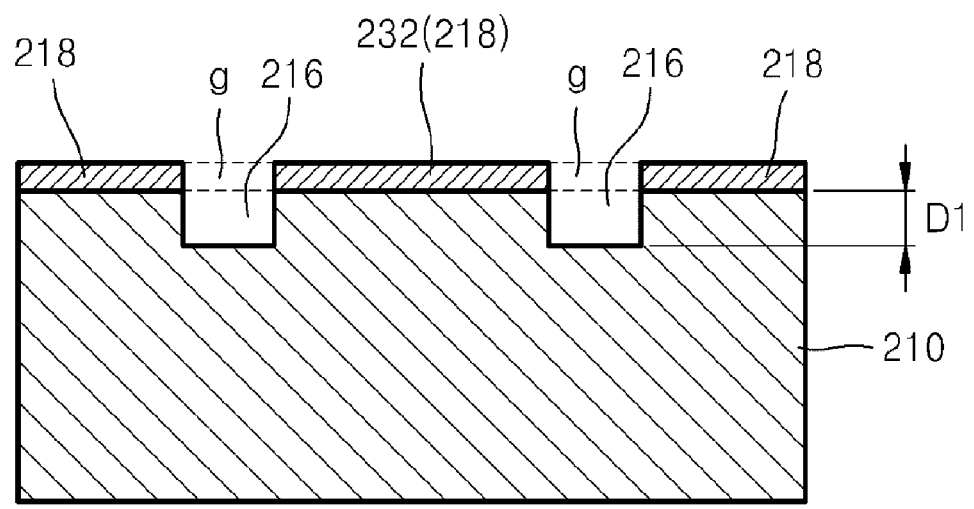

Referring to FIG. 4B, the silicon substrate 210 is exposed by forming gaps g having a predetermined distance, for example, 5 µm, along side surfaces of a cantilever forming region 232. The cantilever forming region 232 may be formed to have a width W2 of approximately 500 µm or less, for example, 10 to 500 µm. Referring to FIG. 4C, grooves 216 having a predetermined depth are formed by primary dry etching of the silicon substrate 210 exposed through the gaps g. The grooves 216 may be formed to have a depth D1 of 1 to 50 µm that corresponds to the thickness of a cantilever.

Figure 4D:
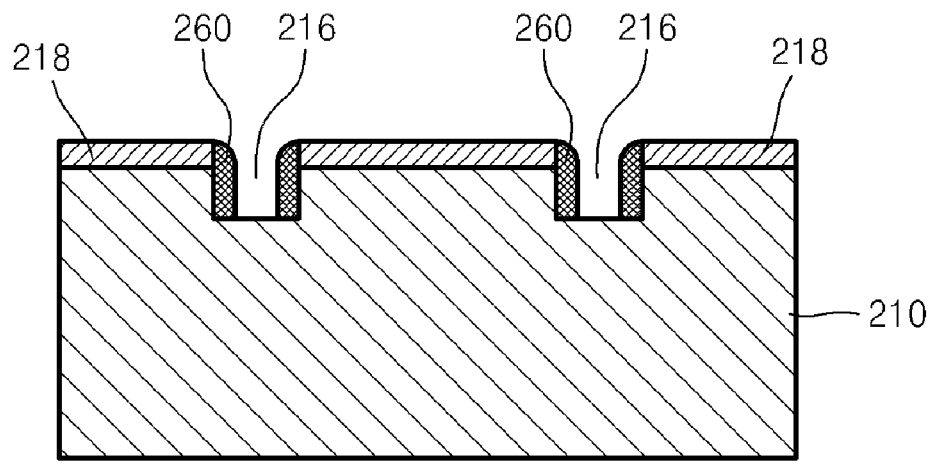

Referring to FIG. 4D, after forming an insulating layer (not shown), for example, a silicon oxide layer on the silicon substrate 210, the insulating layer (not shown) formed on the upper surface of the silicon substrate 210 and the bottoms of the grooves 216 are removed by dry etching of the insulating layer (not shown). As a result, wall protective films 260 are formed along side surfaces of the grooves 216. The wall protective films 260 prevent structure walls (including walls of the cantilevers) from being etched in a subsequent sacrificial layer etching process.

Figure 4E:
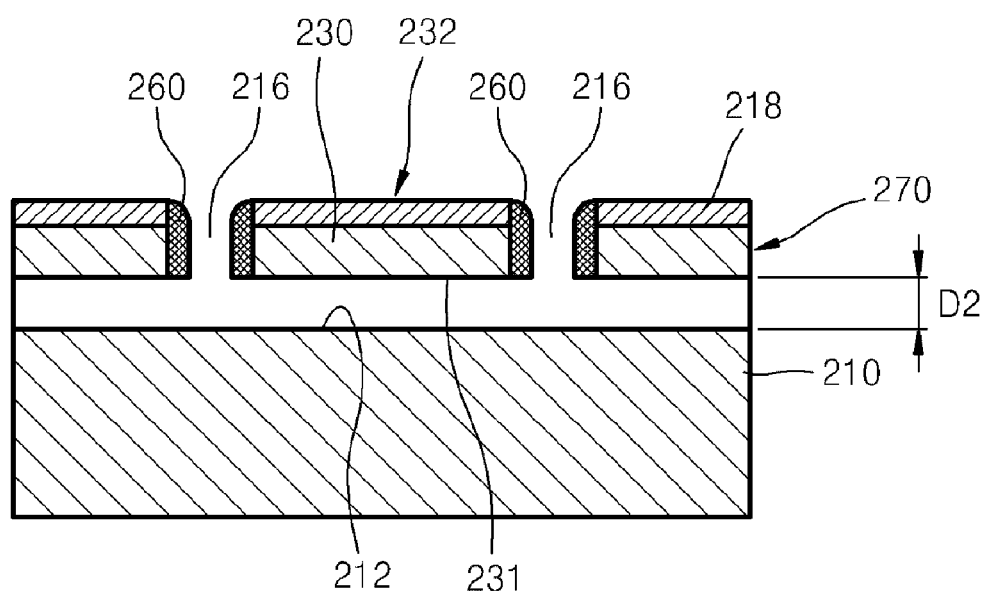

Referring to FIG. 4E, the bottom surfaces of the grooves 216 exposed through the wall protective films 260 are dry etched to a predetermined depth. At this point, the depth of the sacrificial layer, that is, a distance between the bottom surface of the structure (cantilever) and the stopper 212, may be controlled by controlling the depth of etching in a vertical direction.

Afterwards, if anisotropic wet etching is performed, the side walls of the grooves 216 where the wall protective films 260 are formed are not etched, however, portions of the silicon substrate 210 where the wall protective films 260 are not formed are wet etched.

In the present embodiment, since a (111) direction silicon wafer is used, the upper surface of the stopper 212 and a lower surface 231 of the structure 270 are slowly etched using an anisotropic wet etchant such as KOH or TMAH. However, the wet etching proceeds rapidly in a side surface direction, that is, in a perpendicular direction to the (111) crystal surface. Thus, silicon between the lower surface 231 of the structure 270 and the stopper 212 is removed. As a result, a cantilever 230 and the stopper 212 are formed by etching the lower part of the cantilever forming region 232. The distance D2 from the cantilever 230 to the stopper 212 may be 1 to 50 µm. Next, when the insulating layer 218 formed of silicon oxide and the wall protective films 260 formed of silicon oxide are removed by selective etching, the pressure sensor 100 of FIGS. 2 and 3 is fabricated.

According to the method of fabricating a pressure sensor for measuring blood pressure of the present invention, a monolithic pressure sensor with a silicon substrate may be manufactured by etching only upper surface of the substrate. Also, since the etching depth is small, manufacturing time may be short.

Figure 5:
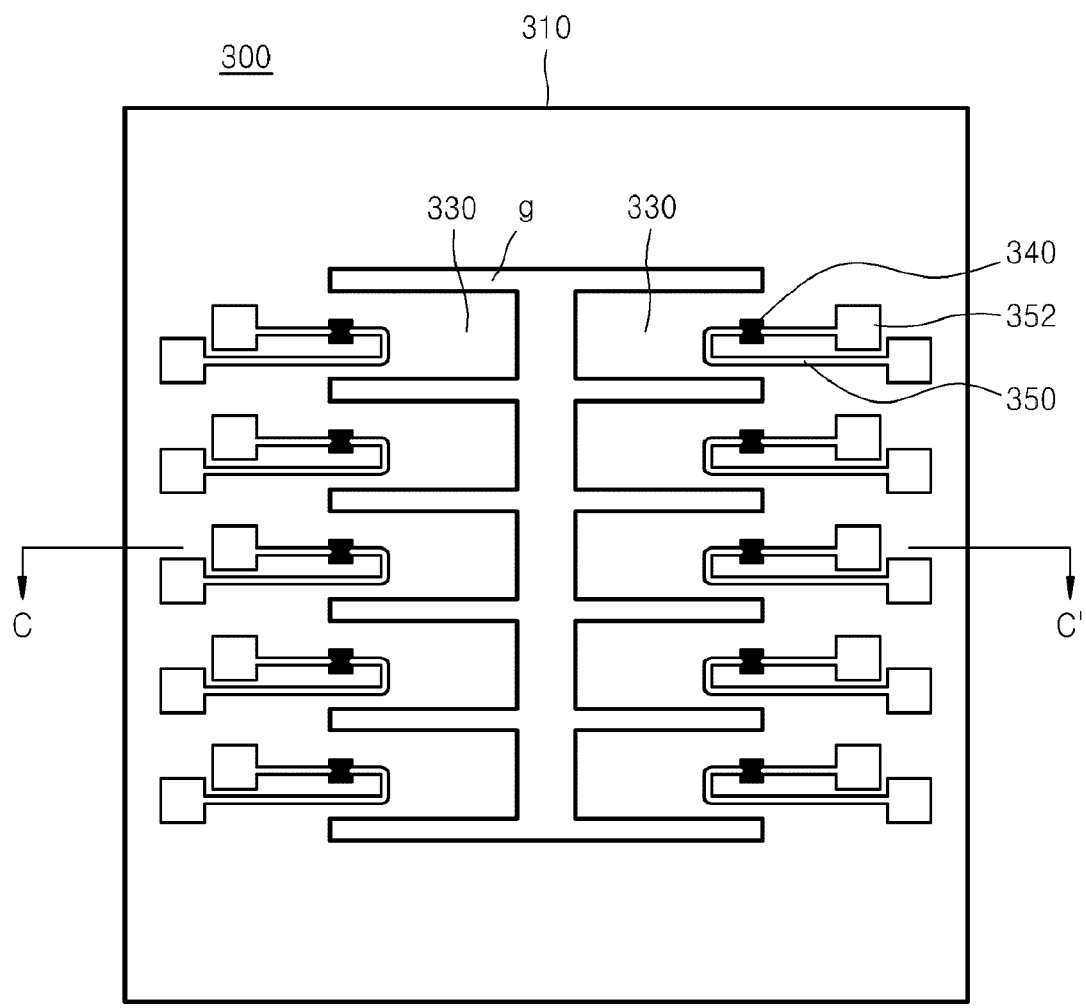
FIG. 5 is a plan view of a pressure sensor for measuring blood pressure, according to another exemplary embodiment of the present invention.
Figure 6:
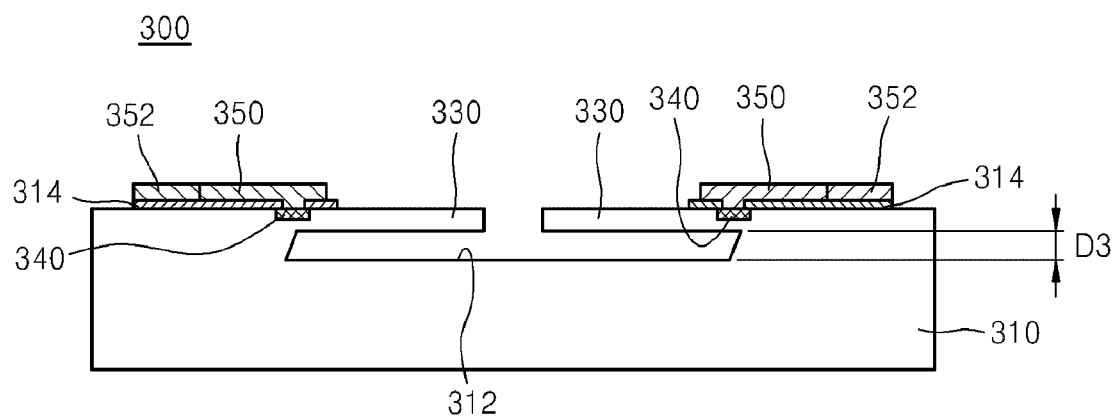
FIG. 6 is a cross-sectional view taken along line C-C' of FIG. 5, according to another exemplary embodiment of the present invention.

FIG. 5 is a plan view of a pressure sensor for measuring blood pressure, according to another exemplary embodiment of the present invention. FIG. 6 is a cross-sectional view taken along line C-C' of FIG. 5. Like reference numerals are used to indicate elements substantially identical to the elements of the pressure sensor 100 of FIGS. 2 and 3, and detailed descriptions thereof will not be repeated.

Referring to FIGS. 5 and 6, five cantilever pairs 330 parallel to each other are formed in an array shape on a silicon substrate 310 and a piezoresistor 340 is formed on a fixed end of each of the cantilevers 330. In the present embodiment, an n-type single crystal silicon substrate 310 having a (111) crystal surface is used, and the piezoresistor 340 may be a boron implanted p-type region. Wires 350, for example, Au or Al wires 350 and electrode pads 352 are connected to both sides of the piezoresistor 340.

The cantilever pairs 330 are parallel to each other, and the cantilever pairs 330 in one row face each other. Gaps g between the cantilever pairs 330 and the silicon substrate 310 may be a few µm, and thus, the dead width, which is a problem in the prior art, may be reduced.

A pressure sensor 300 according to the present embodiment includes stoppers 312 that are formed at locations separated by a predetermined distance D3 from the cantilevers 130 to prevent the cantilevers 330 from excessive deformation. An insulating layer 314 is formed under the wire 350 and the electrode pad 352.

The cantilever pairs 330, the piezoresistors 340, and the stoppers 312 according to the present embodiment are formed using the silicon substrate 310 by applying a semiconductor manufacturing process, and thus, the pressure sensor 300 has a monolithic structure.

Figure 7:
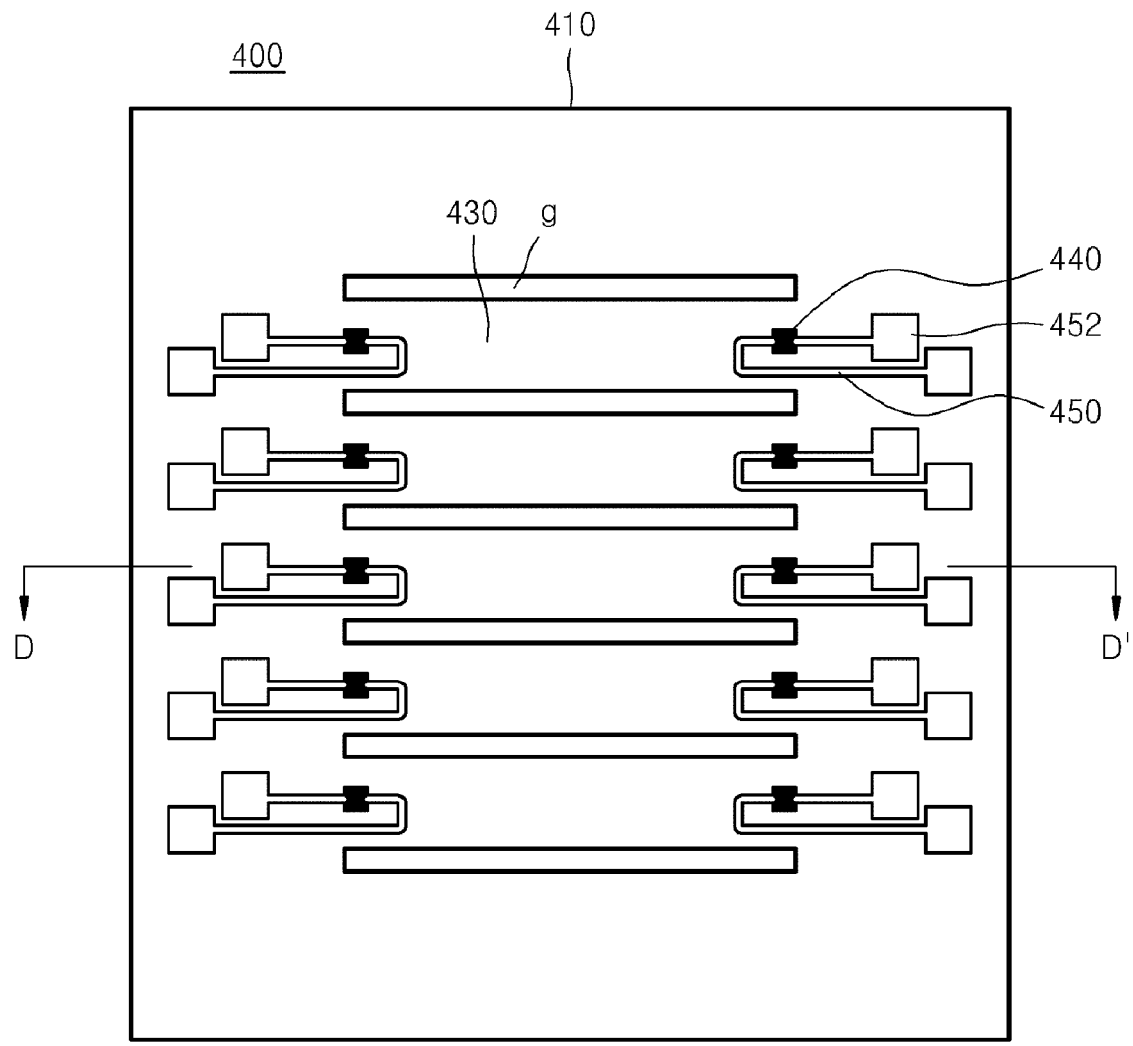
FIG. 7 is a plan view of a pressure sensor for measuring blood pressure, according to another exemplary embodiment of the present invention.
Figure 8:
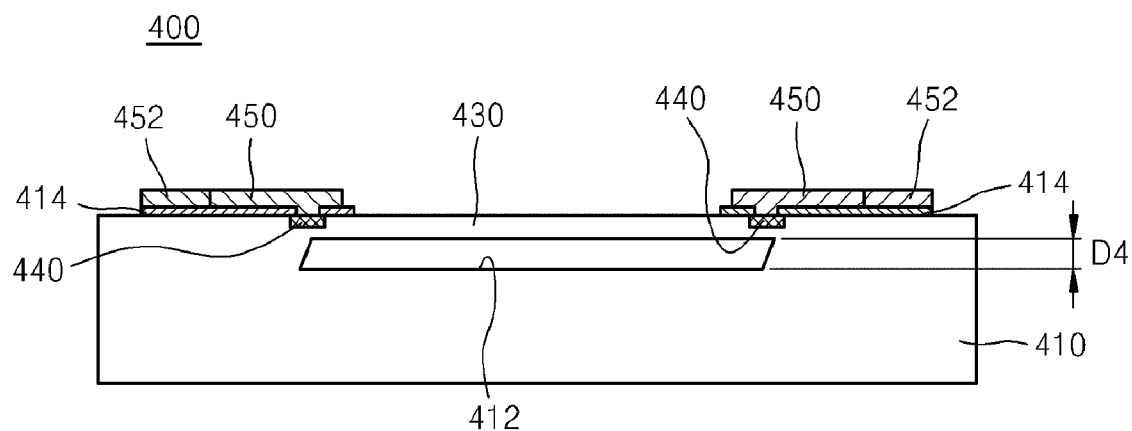
FIG. 8 is a cross-sectional view taken along line D-D' of FIG. 7, according to another exemplary embodiment of the present invention.

FIG. 7 is a plan view of a pressure sensor for measuring blood pressure, according to another embodiment of the present invention, and FIG. 8 is a cross-sectional view taken along line D-D' of FIG. 7. Like reference numerals are used to elements substantially identical to the elements of the pressure sensor 100 of FIGS. 2 and 3, and detailed descriptions thereof will not be repeated.

Referring to FIGS. 7 and 8, five beams 430 parallel to each other are formed in an array shape on a silicon substrate 410, wherein both ends of the beams 430 are supported, and piezoresistors 440 are formed on both ends of each of the beams 430. In the present embodiment, an n-type single crystal silicon substrate 410 is used, and the piezoresistors 440 may be boron implanted p-type regions. Wires 450, for example, Au or Al wires, and electrode pads 452 are connected to both sides of the beams 430.

Gaps g between the beams 430 and the silicon substrate 410 may be equal to a few m, and thus, the dead width, which is a problem in the prior art, may be reduced.

A pressure sensor 400 according to the present exemplary embodiment may include stoppers 412 that are formed at locations separated by a predetermined distance D4 from the lower surface of the beams 430 to prevent the beams 430 from excessive deformation. An insulating layer 414 is formed under the wire 450 and the electrode pad 452.

The beams 430, the piezoresistors 440, and the stoppers 412 according to the present embodiment are formed using the silicon substrate 410 by applying a semiconductor manufacturing process, and thus, the pressure sensor 400 has a monolithic structure.

The pressure sensor 300 of FIGS. 5 and 6 and the pressure sensor 400 of FIGS. 7 and 8 have shapes of a cantilever or a beam supported at both ends, which is different from the pressure sensor 100 of FIGS. 2 and 3; however, the pressure sensors 300 and 400 may be manufactured using substantially the same method like in the case of the pressure sensor 100, and thus, detailed description thereof will not be repeated.

As described above, a blood pressure measuring apparatus according to the present invention has a monolithic structure in which stoppers prevent sensing units from excessive deformation, and the sensing units, the stoppers, and the substrate are formed in one unit.

Also, an array type pressure sensor for measuring blood pressure according to present invention has small gaps between the sensing units, thus, a dead width may be reduced, thereby being possible to precisely and consecutively measure the blood pressure.

According to a method of fabricating the pressure sensor for measuring blood pressure of the present invention, processing is performed on an upper part of a silicon substrate and an etching depth is relatively small, thus, a fabricating process is simple. In particular, a portion between lower parts of the sensing units and the stoppers may be readily etched using a single crystal silicon having a (111) crystal surface.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A pressure sensor for measuring blood pressure, comprising:
    at least one cantilever formed on an upper surface of a silicon substrate;
    a piezoresistor formed on a fixed end of the cantilever; and
    a metal wire and an electrode pad connected to both ends of the piezoresistor,
    wherein a stopper that limits a deformation of a free end of the cantilever is formed below the cantilever,
    wherein the cantilever comprises a plurality of cantilevers, and the plurality of cantilevers are parallel to each other, and
    wherein the plurality of cantilevers are formed on the silicon substrate so that each cantilever extends in an opposite direction with respect to an adjacent cantilever.

2. The pressure sensor of claim 1, wherein the silicon substrate is a single crystal silicon having a (111) crystal surface on an upper surface thereof.

3. The pressure sensor of claim 1, wherein each cantilever has a width of 10 to 500 μm.

4. The pressure sensor of claim 1, wherein a depth from each cantilever to the stopper is 1 to 50 μm.

5. The pressure sensor of claim 1, wherein the plurality of cantilevers comprises at least one pair of cantilevers disposed in a row along their longitudinal direction so as to face each other.

6. The pressure sensor of claim 1, wherein the silicon substrate, the cantilevers, and the stopper are formed in a monolithic structure.

7. A method of fabricating a pressure sensor, comprising:
    (a) forming a piezoresistor on a fixed end of cantilever forming region on an upper surface of a silicon substrate;
    (b) forming a wire and an electrode pad connected to both ends of the piezoresistor;
    (c) forming an insulating layer on the silicon substrate that exposes a first region that defines the cantilever forming region;
    (d) etching the silicon substrate to a predetermined depth from a surface of the first region of the silicon substrate;
    (e) forming a wall protective film on a side wall of the etched first region;
    (f) forming a first wall where the wall protective film is not formed by dry etching the first region of the silicon substrate exposed through the wall protective film to a predetermined depth; and
    (g) forming a cantilever that is supported at one end by the silicon substrate and a stopper that limits a deformation of the cantilever by etching the first wall exposed through the wall protective film.

8. The method of claim 7, wherein the silicon substrate is a single crystal silicon having a (111) crystal surface on an upper surface thereof.

9. The method of claim 7, wherein the forming of the piezoresistor comprises implanting a p-type dopant in the fixed end of the cantilever forming region.

10. The method of claim 7, wherein the cantilever has a width of 10 to 500μm.

11. The method of claim 7, wherein a distance from a lower surface of the cantilever to an upper surface of the stopper is 1 to 50 μm.

12. The method of claim 7, wherein a distance from a lower surface of the beam to an upper surface of the stopper is 1 to 50 μm.

13. A method of fabricating a pressure sensor, comprising:
    (a) forming piezoresistors on both ends of a beam forming region on an upper surface of a silicon substrate;
    (b) forming a wire and an electrode pad connected to both ends of each of the piezoresistors;
    (c) forming an insulating layer that exposes a first region that defines the beam forming region on the silicon substrate;
    (d) etching the silicon substrate to a predetermined depth from a surface of the first region of the silicon substrate;
    (e) forming a wall protective film on a side wall of the etched first region;
    (f) forming a first wall where the wall protective film is not formed by dry etching the first region of the silicon substrate exposed through the wall protective film to a predetermined depth; and
    (g) forming a beam that is supported at both ends by the silicon substrate and a stopper that limits a deformation of the beam by etching the first wall exposed through the wall protective film.

14. The method of claim 13, wherein the silicon substrate has a (111) crystal surface.

15. The method of claim 13, wherein the forming of the piezoresistor comprises implanting a p-type dopant in the both ends of the beam forming region.

16. The method of claim 13, wherein the beam has a width of 10 to 500 μm.

* * * * *